United States Patent [19]

Nakao et al.

[11] 4,456,007
[45] Jun. 26, 1984

[54] INHALER

[75] Inventors: Shinroku Nakao, Kanagawa; Yoshiyasu Ishii; Kazuo Nagata, both of Tokyo, all of Japan

[73] Assignee: Combi Co., Ltd., Tokyo, Japan

[21] Appl. No.: 329,108

[22] Filed: Dec. 9, 1981

[30] Foreign Application Priority Data

Dec. 12, 1980 [JP] Japan .......................... 55-178213[U]
Dec. 12, 1980 [JP] Japan .......................... 55-178214[U]
Jan. 29, 1981 [JP] Japan ............................ 56-11335[U]

[51] Int. Cl.³ ............................................. A61M 11/04
[52] U.S. Cl. .......................... 128/200.21; 128/203.16; 239/138; 222/533
[58] Field of Search ..................... 128/200.14, 200.16, 128/200.17, 200.18, 200.21, 200.23, 367, 203.16; 222/533, 534, 535, 539; 604/58; 239/138, 369, 338

[56] References Cited

U.S. PATENT DOCUMENTS

| 3,010,223 | 11/1961 | Alderson | 46/161 |
| 3,622,053 | 11/1971 | Ryden | 121/200.23 |
| 3,809,086 | 5/1974 | Deaton | 128/200.18 |
| 4,300,546 | 11/1981 | Kruber | 128/200.16 |
| 4,318,397 | 3/1982 | Kobayashi | 128/200.21 |

FOREIGN PATENT DOCUMENTS 167807 12/1904 Fed. Rep. of Germany ....................... 128/200.21

Primary Examiner—Henry J. Recla
Assistant Examiner—Karin M. Reichle
Attorney, Agent, or Firm—Sughrue, Mion, Zinn, Macpeak and Seas

[57] ABSTRACT

An inhaler comprises a vapor producing unit, and a cover incorporating a vapor feeding nozzle. The vapor feeding nozzle is pivotally mounted on the cover in such a manner that the vapor feeding nozzle can be tilted at a desired angle. Also, a novel construction of an inner mechanism for the inhaler is disclosed.

6 Claims, 5 Drawing Figures

INHALER

BACKGROUND OF THE INVENTION

This invention relates to an inhaler having a novel construction.

A variety of inhalers which are so designed that chemical vapors together with steam are jetted to maintain one's health or to cure the throat are known in the art. However, these conventional inhalers are disadvantageous in the following point. Since the vapor feeding sleeve for guiding a stream of mixed chemical vapors is set at a fixed angle, the user must set himself so as to be in agreement with the angle of the vapor feeding sleeve thereby to introduce the stream of vapors to his throat. Thus, his posture is not natural in using the inhaler.

On the other hand, in producing a chemical vapor with an ordinary inhaler, a chemical is sucked into a stream of steam jetted by a vapor producing unit. The inhaler has a chemical container and a condensed water container in addition to the vapor producing unit.

However, the conventional inhaler suffers from the following difficulty: Since no protective means is provided for the chemical container or a chemical sucking nozzle inserted into the chemical container, steam deposited on the chemical sucking nozzle flows down into the chemical container, to dilute the chemical in the chemical container.

SUMMARY OF THE INVENTION

The present invention is intended to overcome the above-described drawbacks accompanying a conventional inhaler, by providing an inhaler as described below.

An object of the invention is to provide an inhaler which is so designed that its vapor feeding sleeve is set out of the cover only when the inhaler is used, and it is set in the cover when it is not in use.

Another object of the invention is to provide an inhaler which is so designed that the vapor feeding sleeve can be tilted at a desired angle in using the inhaler.

Still another object of the invention is to provide a nozzle mechanism for an inhaler which is so designed as to protect a chemical from being diluted by water condensed from jetted steam.

PREFERRED EMBODIMENTS OF THE INVENTION

Figure 1:
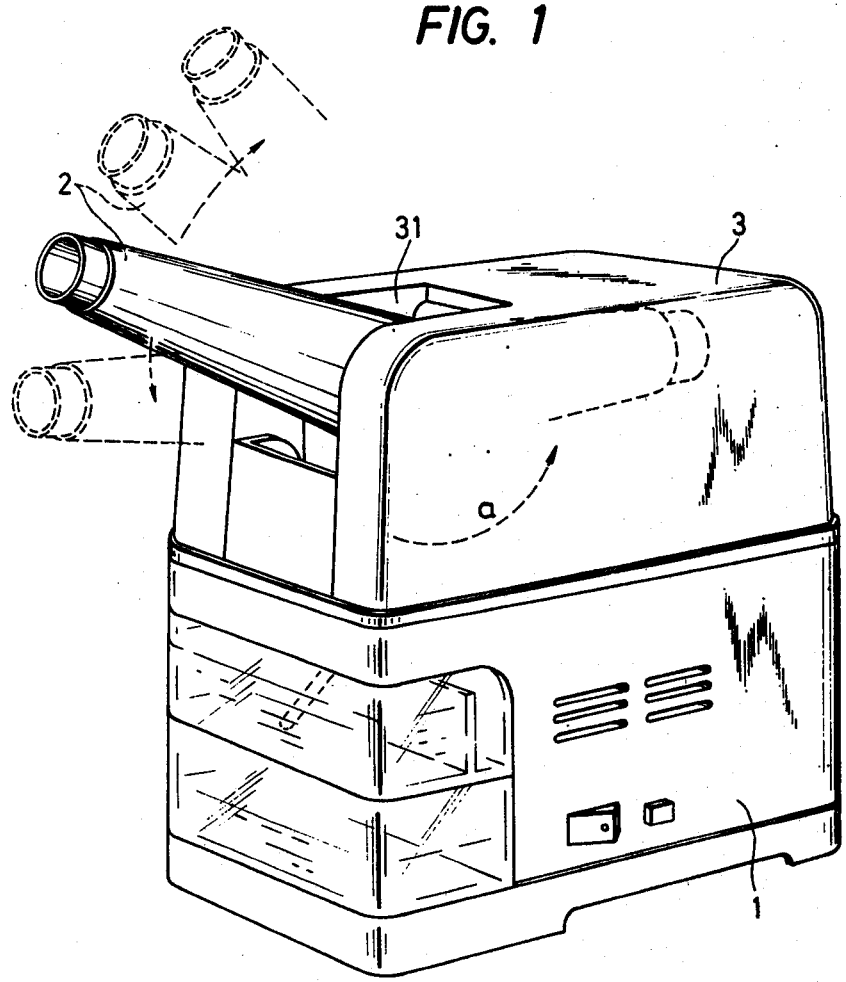
FIG. 1 is a perspective view of an inhaler according to the present invention.
Figure 2:
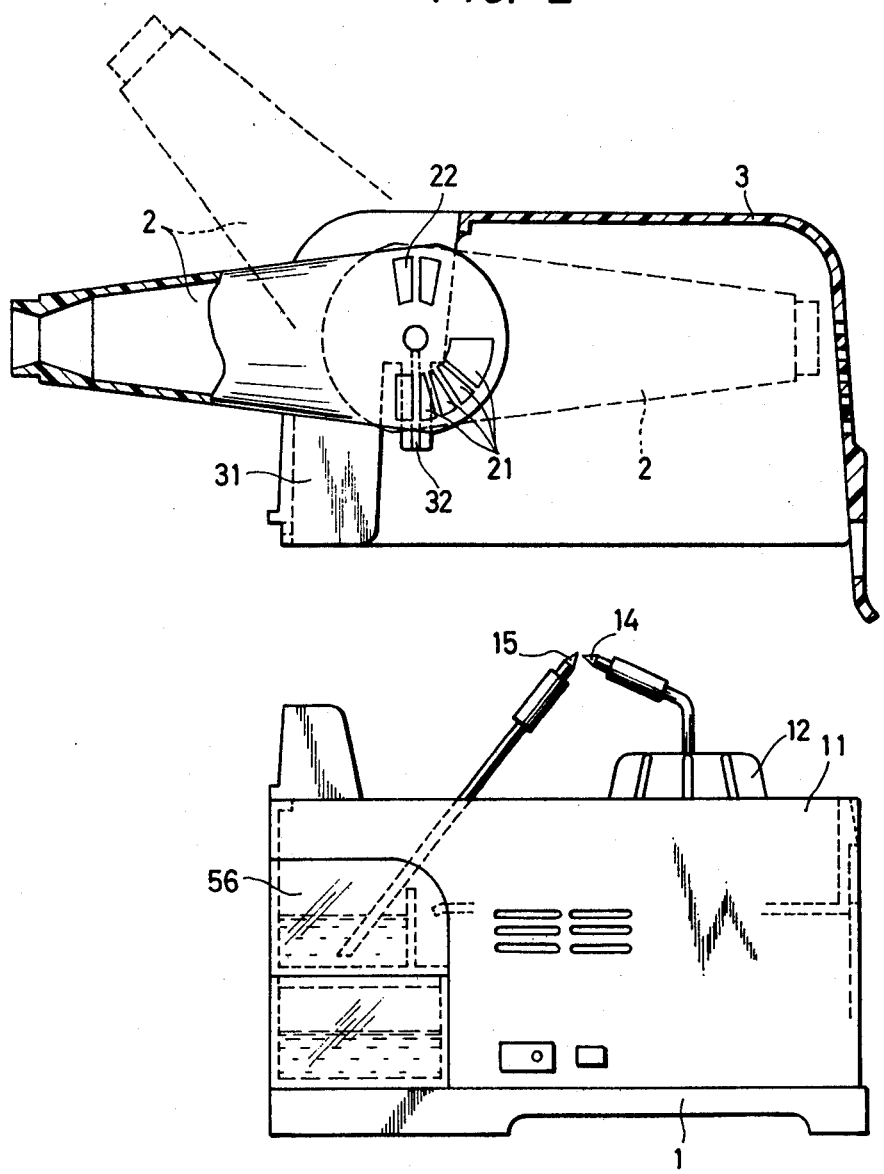
FIG. 2 is an exploded view of an inhaler body and its cover, with a part of the cover sectioned.
Figure 3:
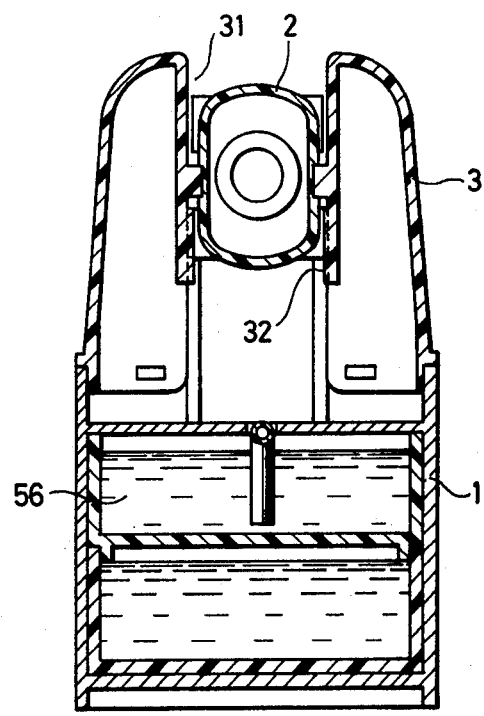
FIG. 3 is a vertical sectional view of the inhaler shown in FIG. 1.

One embodiment of this invention will be described with reference to the accompanying drawings. An inhaler according to the invention comprises: a vapor producing unit body 1 an inner construction of which will be described in detail later; and a cover 3 having a rotatable vapor feeding sleeve 2 adapted to feed a mixed chemical vapor, in combination. It is preferable that the cover 3 be made of plastic. The vapor producing unit body 1 has a housing 11 on which a vapor producing unit 12 and a chemical container 56 are provided. The vapor producing unit 12 an inner mechanism of which is well known in the art is provided with a vapor jetting nozzle 14 and a chemical sucking nozzle 15. The cover 3 is detachably fitted in the upper opening of the vapor producing unit body 1. A nozzle path opening 31 is formed in the front portion of the cover 3. The mixed chemical vapor feeding sleeve 2 is pivotably mounted in the opening 31 in such a manner that it can be tilted at a desired angle. The sleeve 2 is substantially in the form of a tapered cylinder the diameter of which is gradually reduced towards the outer end. Locking grooves 21 and a locking groove 22 which is used when the nozzle is turned in an opposite direction are formed radially in each side wall of the sleeve 2 is near the sleeve base, in such a manner that a selected one of the grooves is engaged with a locking strip 32 which is protruded from each side inner wall of the cover 3. It is desirable that the locking strip 32 be protruded from the inner wall of the cover 3 to the extent that the height of protrusion of the locking strip 32 will not obstruct the rotation of the vapor feeding sleeve 2, for instance to 0.5 to 1 mm. Since each locking strip 32 is formed on a wall extending downwardly from the inner side wall of the cover 3 made of synthetic resin, the locking strip 32 is firmly engaged with the selected groove 21 or 22 formed in the side wall of the sleeve 2.

As is apparent from the above description, according to the present invention, the angle of inclination of the vapor feeding sleeve 2 can be changed. Therefore, the user can set the vapor feeding sleeve at a suitable angle so that the vapor is naturally applied to the throat of the user who sits on the chair, in advance. Accordingly, even if he uses the inhaler for a long time, he will never become fatigued because his posture is natural in using the inhaler. After the inhaler has been used, the sleeve 2 is turned in the direction of the arrow a in FIG. 1 until the locking groove 22 is engaged with locking strip 32, so that the sleeve 2 is stably held in the cover 3. Therefore, the vapor feeding sleeve 2 for applying the mixing chemical vapor to the throat can be held sanitarily.

Figure 4:
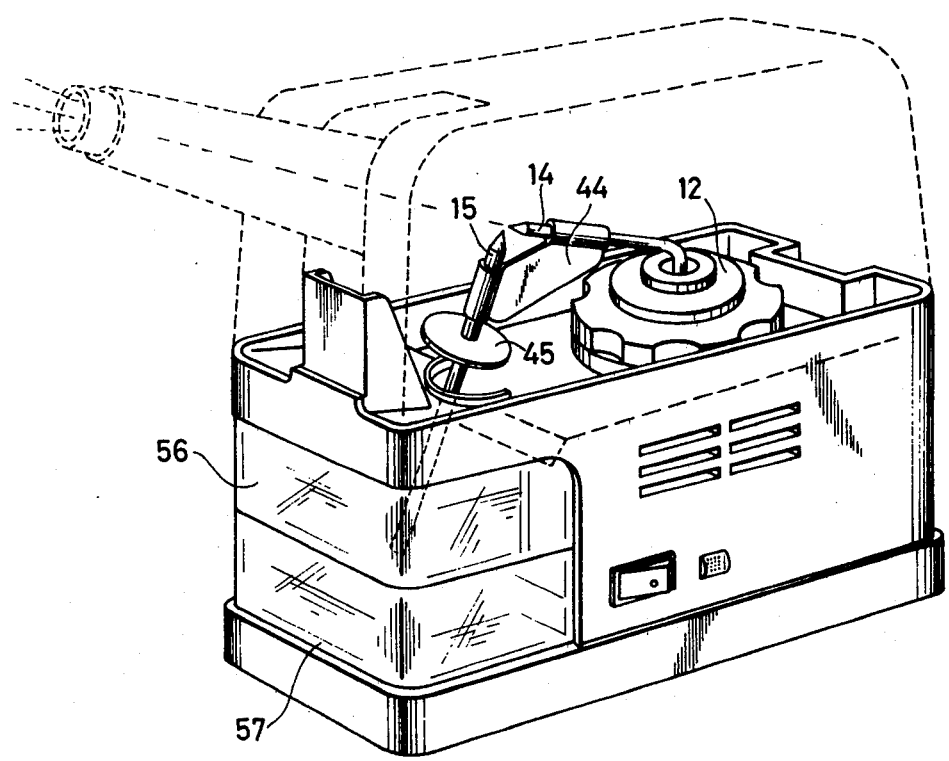
FIG. 4 is a perspective view of the inhaler from which the cover has been removed.
Figure 5:
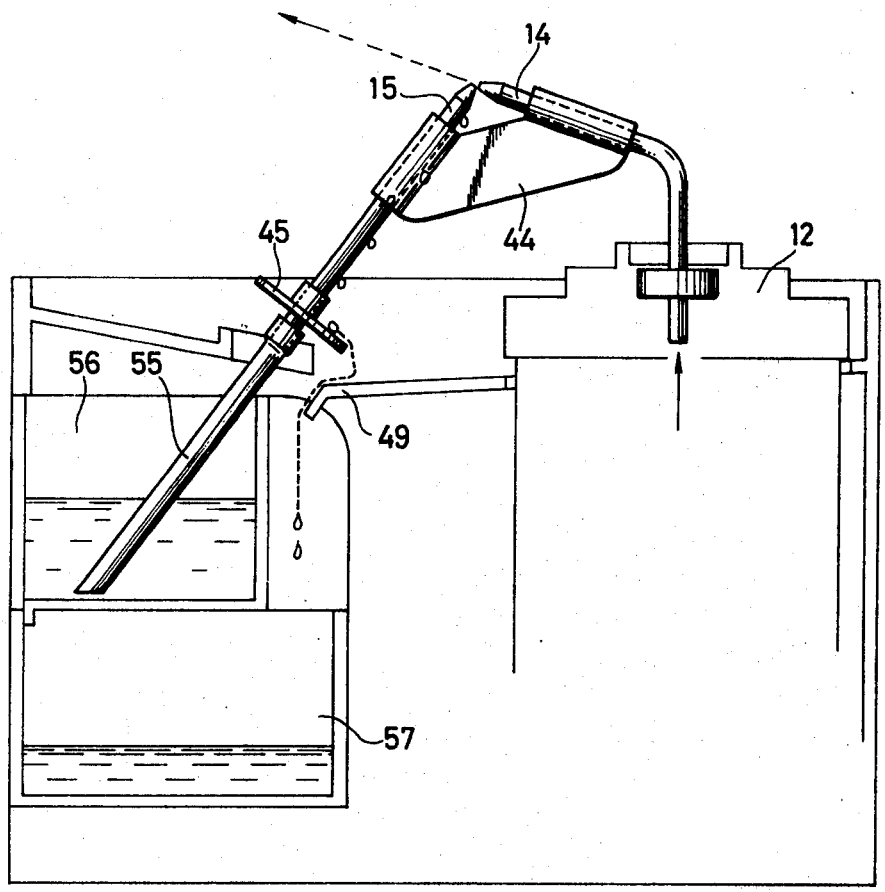
FIG. 5 is a side view of the essential components of the inhaler shown in FIG. 4.

A preferred construction of an inner mechanism of the vapor producing unit body 1 will now be described in detail with reference to FIGS. 4 and 5. In FIGS. 4 and 5, the vapor jetting nozzle 14 communicates through its base with a vapor producing unit 12 and the top end of the chemical sucking nozzle 15 is confronted with the top end of the vapor jetting nozzle 14 by means of an arm plate 44. A water bypassing flange 45 is secured to the base of the chemical sucking nozzle 15. The flange 45 extends radially from the base of the nozzle 15 to a suitable dimension. Further, in FIG. 5, reference numeral 55 designates a tube of rubber or the like one end of which is coupled to the lower end portion of the chemical sucking nozzle 15, with the other end inserted into a chemical container 56; and 57, a container into which condensed water drops.

As described above, the water bypassing flange 45 is provided integral with the base of the chemical sucking nozzle 15 according to the invention. Therefore, as shown in FIG. 5, water reduced from the steam in the inhaler, which otherwise would flow down the sucking nozzle 15 into the chemical container 56, is directed towards the reduced water receiving container 57 by the water bypassing flange 45 in association with a deflector 49. Thus, the chemical in the chemical container 56 will never be diluted by the condensed water.

Only one preferred embodiment of the invention has been described. It is apparent that various modifications are possible within the scope of the accompanying claims.

What is claimed is:

1. An inhaler comprising a body having a vapor producing unit therein, cover means detachably fitting on said body and having aperture means therein, a vapor feeding sleeve for directing a vapor into a user's mouth, and pivot means for pivotally mounting said vapor feeding sleeve on said cover means for movement between a first plurality of positions wherein said sleeve extends outwardly through said aperture means at a desired angle and a second position wherein said sleeve is disposed completely within said cover, said aperture means permitting pivotal movement of said sleeve between said first and second positions only when said cover means is removed from said body.

2. An inhaler as claimed in claim 1 wherein said vapor producing unit includes a vapor jetting nozzle and a chemical jetting nozzle, said vapor jetting nozzle and said chemical jetting nozzle are coupled to each other by a connecting arm member so that said vapor jetting nozzle and said chemical jetting nozzle confront each other to define a predetermined angle.

3. An inhaler as claimed in claim 2, wherein said chemical nozzle has a water bypass flange, said vapor producing body further including a chemical container and a condensed water receiving container, said water bypass flange being so positioned that condensed water may be collected into said condensed water receiving container.

4. An inhaler as claimed in claim 1, wherein said pivot means for mounting includes a plurality of locking grooves and a locking strip engageable with selected one of said locking grooves.

5. An inhaler as claimed in claim 4, wherein said locking grooves are formed in said vapor feeding sleeve and said locking strip is formed on said cover.

6. An inhaler as claimed in claim 5, wherein said locking grooves include a single locking groove engaged with said locking strip when the vapor feeding sleeve is rotated inwardly and received in said cover.

* * * * *